(12) United States Patent
Gumlich et al.

(10) Patent No.: US 7,834,211 B2
(45) Date of Patent: Nov. 16, 2010

(54) METHOD FOR PRODUCING TETRACARBOXYLIC ACIDS

(75) Inventors: Kai Gumlich, Mannheim (DE); Joaquim Henrique Teles, Otterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 255 days.

(21) Appl. No.: 11/911,686

(22) PCT Filed: Apr. 27, 2006

(86) PCT No.: PCT/EP2006/061887
§ 371 (c)(1),
(2), (4) Date: Oct. 16, 2007

(87) PCT Pub. No.: WO2006/117326
PCT Pub. Date: Nov. 9, 2006

(65) Prior Publication Data
US 2009/0124827 A1 May 14, 2009

(30) Foreign Application Priority Data
Apr. 29, 2005 (DE) .................. 10 2005 020 494

(51) Int. Cl.
*C07C 55/00* (2006.01)
(52) U.S. Cl. .................................... 562/590
(58) Field of Classification Search ............ None
See application file for complete search history.

(56) References Cited

U.S. PATENT DOCUMENTS

| 2,557,282 A | * | 6/1951 | Hamblet et al. ............ 562/529 |
| 5,047,582 A | * | 9/1991 | Brotherton et al. ......... 562/508 |
| 5,157,152 A | | 10/1992 | Brotherton et al. |

FOREIGN PATENT DOCUMENTS

| DE | 30 16 225 | | 10/1981 |
| EP | 0 039 048 | | 11/1981 |
| EP | 0 354 648 | | 2/1990 |
| EP | 0 688 897 | | 12/1995 |
| JP | 05-178788 A | * | 7/1993 |
| NL | 6601148 | | 1/1966 |

OTHER PUBLICATIONS

Franz, John E., "Mechanism of the Nitric Acid Oxidation of Olefins", J. Org Chem., vol. 30, pp. 1488-1491, 1965.
* cited by examiner

*Primary Examiner*—Paul A Zucker
(74) *Attorney, Agent, or Firm*—Oblon, Spivak, McClelland, Maier & Neustadt, L.L.P.

(57) ABSTRACT

A process for preparing tetracarboxylic acids of the general formula I

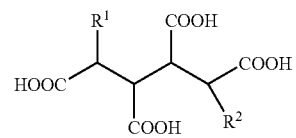

or salts thereof, wherein at least one compound of the general formula II a or II b

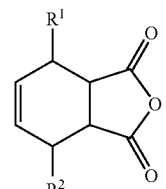

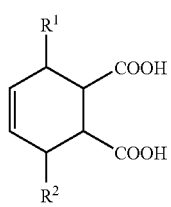

(a) is first reacted with at least one epoxidation reagent and (b) then oxidized with nitric acid or at least one nitrogen oxide,
where the variables are defined as follows:
$R^1$, $R^2$ are the same or different and are selected from hydrogen, phenyl and $C_1$-$C_{10}$-alkyl.

9 Claims, No Drawings

METHOD FOR PRODUCING TETRACARBOXYLIC ACIDS

The present invention relates to a process for preparing tetracarboxylic acids of the general formula I

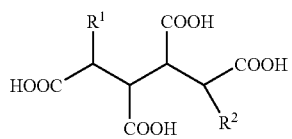

or salts thereof, wherein at least one compound of the general formula II a or II b

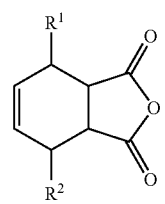

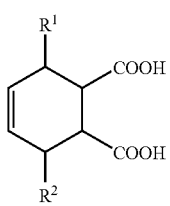

(a) is first reacted with at least one epoxidation reagent and (b) then oxidized with nitric acid or at least one nitrogen oxide, where the variables are defined as follows:

$R^1$, $R^2$ are the same or different and are selected from hydrogen, phenyl and $C_1$-$C_{10}$-alkyl.

Tetracarboxylic acids have recently found numerous applications not only generally as involatile organic acids, but also as an agent for formaldehyde-free finishing and in particular for formaldehyde-free anticrease finishing of textiles; see, for example, EP-A 0 354 648.

Processes known to date for preparing tetracarboxylic acids are typically based on the oxidation of Diels-Alder adducts of dienes, for example butadiene, and of dicarboxylic anhydrides, for example maleic anhydride. However, known processes generally have disadvantages. For instance, U.S. Pat. No. 5,157,152 describes a two-stage process for the oxidation of, for example, tetrahydrophthalic acid to butane-1,2,3,4-tetracarboxylic acid by double reaction with hydrogen peroxide at in each case from 80 to 115° C., 4,5-dihydroxyhexahydrophthalic acid being formed as an intermediate. However, it is only be removed with difficulty and that the reaction is incomplete. 4,5-dihydroxyhexahydrophthalic acid, known as glycol, remains in a significant proportion in the product. It is also necessary to use a large amount of hydrogen peroxide. Thus, at least 4.1 equivalents of hydrogen peroxide are required in order to oxidize 4,5-dihydroxyhexahydrophthalic acid to butane-1,2,3,4-tetracarboxylic acid.

J. E. Franz et al., *J. Org. Chem.* 1965, 30, 1488 disclose that cis-$\Delta^4$-tetrahydrophthalic acid can be oxidized in a one-stage process to butane-1,2,3,4-tetracarboxylic acid by adding cis-$\Delta^4$-tetrahydrophthalic acid to a solution of ammonium metavanadate in concentrated nitric acid (examples: right-hand column, page 1491). However, the yield of butane-1,2,3,4-tetracarboxylic acid can be improved.

DE 30 16 225 discloses that, for example, butane-1,2,3,4-tetracarboxylic acid which has been obtained by oxidation of $\Delta^4$-tetrahydrophthalic acid with ammonium metavanadate in concentrated nitric acid in a one-stage process is typically contaminated with nitro compounds and nitrogen compounds (page 3, line 19 ff., page 4, line 5 ff.) which can be disruptive in the course of later use. For example, such impurities lead in the course of esterification to undesired brown coloring. DE 30 16 225 shows that, for example, butane-1,2,3,4-tetracarboxylic acid can be purified by aftertreatment with nitric acid for several hours. However, such a process is time-consuming, and the yield of 66.5% is capable of improvement.

It was thus an object of the invention to provide a process which affords tetracarboxylic acids in good purity and good yield with an acceptable level of complexity and expense. It was a further object to provide tetracarboxylic acids in such good purity that they are suitable for use for the anticrease finishing of textiles.

Accordingly, the process defined at the outset has been found.

The process according to the invention starts from one or more compounds of the general formula II a or II b

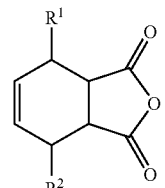

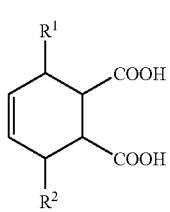

in which the variables are defined as follows:

$R^1$, $R^2$ are different or preferably the same and are selected from phenyl, $C_1$-$C_{10}$-alkyl, branched or preferably unbranched, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl, more preferably unbranched $C_1$-$C_4$-alkyl such as methyl, ethyl, n-propyl, n-butyl, and more preferably hydrogen.

Most preferably, $R^1$ and $R^2$ are the same and are each hydrogen.

To carry out the process according to the invention, it is also possible to start from mixtures of at least one compound of the formula II a and at least one compound of the formula II b. For example, it is possible to start from mixtures of

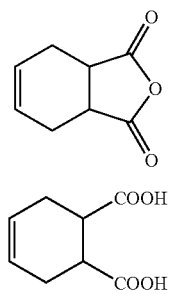

In compounds of the general formula II b, the relative stereochemistry of the two carboxyl groups to one another is open. The two carboxyl groups are preferably in cis configuration relative to one another.

Compounds of the general formula II a and II b are known as such and obtainable by methods known per se, for example by Diels-Alder reaction of dienes and dicarboxylic acids or their anhydrides.

In step (a), at least one compound of the general formula II a or II b is first reacted with at least one epoxidation reagent.

Suitable epoxidation reagents are in particular peroxides, for example organic peroxides such as tert-butyl hydroperoxide and meta-chloroperbenzoic acid, and most preferably hydrogen peroxide. When hydrogen peroxide is to be used, it is used, for example, in the form of an aqueous solution, for example as a from 10 to 70% by weight aqueous solution, more preferably as a from 30 to 50% by weight aqueous solution.

It is possible to use epoxidation reagent (a) in an equimolar amount based on compound of the general formula II a or II b.

In step (a), epoxidation reagent is preferably used in an excess. This means an excess based on compound of the general formula II a or II b. Suitable excesses are in particular from 5 mol % to 300 mol %, preferably from 100 to 150 mol %.

Compound of the general formula II a or II b can be reacted with epoxidation reagent in step (a), for example, at a temperature in the range from 30 to 150° C., preferably from 60 to 105° C., more preferably from 70 to 90° C.

Compound of the general formula II a or II b can be reacted with epoxidation reagent in step (a) preferably at standard pressure. However, it is also possible to work under elevated pressure, for example from 1.1 to 5 bar.

Compound of the general formula II a or II b can be reacted with epoxidation reagent in step (a), for example, over a period of from 30 minutes to 10 hours; preference is given to from one to five hours.

The sequence of addition of compound of the general formula II a or II b and epoxidation reagent is uncritical per se. In one embodiment of the present invention, the procedure is to mix compound of the general formula II a or II b with an inert diluent if appropriate, to initially charge and to admix with epoxidation reagent.

For the reaction of compound of the general formula II a or II b with epoxidation reagent in step (a), the procedure in one embodiment of the present invention is first to mix compound of the general formula II a or II b with an inert diluent, in particular with water, for example with from 10 to 1000% by weight of water based on compound of the general formula II a or II b. For mixing, it is possible to work, for example, at temperatures in the range from 20 to 150° C., preferably from 80 to 100° C.

In one embodiment of the present invention, step (a) is performed using at least one catalyst. Suitable catalysts are, for example, Brønsted acids, tungstates, molybdates, heterpoly compounds of molybdenum or tungsten and in particular molybdenum or tungsten compounds, for example sodium molybdate or ammonium tungstate. Preference is given to working in step (a) without catalyst.

The heat of reaction from step (a) can be removed, for example, by indirect cooling or by partially or fully distilling off inert diluent and/or water formed during the reaction.

The reaction in step (a) initially affords epoxide of the general formula III a or III b

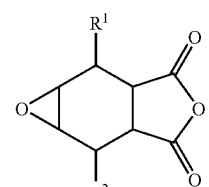

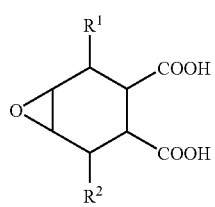

for example as a mixture, especially as regards the configuration of the epoxide relative to the anhydride moiety or the carboxyl groups, and the $R^1$ and $R^2$ radicals in the case that $R^1$ and $R^2$ are not both hydrogen. When working in the presence of water, anhydride moiety and epoxide are typically hydrolyzed in situ, for example partially or even quantitatively, to obtain compound of the general formula IV

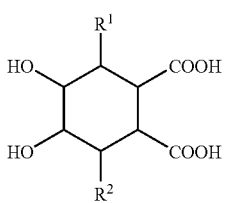

in which the hydroxyl groups are typically trans to one another, which is also referred to hereinbelow as intermediate.

Compound of the general formula IV can be isolated. However, preference is given to dispensing with an isolation and thus purification of compound of the general formula IV. In one embodiment of the present invention, step (b) follows step (a) without isolation of intermediate.

In step (b), oxidation is effected with nitric acid, for example from 20 to 100% by weight aqueous nitric acid, preferably with from 50 to 70% by weight, more preferably from 65 to 68% by weight, aqueous nitric acid, or with at least one nitrogen oxide, for example $N_2O_5$.

Step (b) can be carried out without catalyst.

In one variant of the present invention, oxidation is effected in step (b) in the presence of at least one catalyst.

In the context of the present invention, catalyst can be one or more dissolved compounds which are soluble in nitric acid and which can be metered separately or together with nitric acid. In one variant of the present invention, catalyst for step (b) can also be metered as early as at the start of step (a).

In the context of the present invention, catalysts are preferably tungsten-free, i.e. they are compounds of, for example, manganese and more preferably vanadium. When tungsten is present as an impurity in catalyst used in step (b) in accordance with the invention, the content of tungsten does not exceed 10% by weight of catalyst. Most preferably, catalyst in the context of the present invention is one or more compounds which comprise(s) vanadium.

In one embodiment of the present invention, preference is given to using, in step (b), a mixed catalyst which comprises a catalytically active main component, for example a vanadium compound, and a cocatalyst which, taken as a sole catalyst, only has low catalytic activity. Suitable cocatalysts are in particular iron and copper salts, for example $FeCl_3$, $CuSO_4$ and $CuCl_2$.

In one embodiment of the present invention, a compound is used which comprises at least one atom of vanadium per molecule together with from 1 to 1.5 molar equivalents of cocatalyst based on vanadium compound, for example $FeCl_3$, or copper salts, for example $CuSO_4$ or $CuCl_2$.

It is possible, for example, to use vanadium compounds in which vanadium is present in any oxidation state, but preferably in the +5 oxidation state.

Particularly preferred catalysts are heteropolyacids of vanadium and ammonium metavanadate.

In one embodiment of the present invention, in the range from 0.001 to 1% by weight, preferably from 0.01 to 0.1% by weight and more preferably from 0.03 to 0.05% by weight, of catalyst is used, based on compound of the general formula II a or II b.

To initiate the oxidation in step (b), it is possible to add at least one initiator. Suitable initiators are, for example, potassium nitrite and more preferably sodium nitrite. For example, from 0.01 to 0.1% by weight of initiator can be added, based on compound of the general formula II a or II b; preference is given to from 0.03 to 0.05% by weight.

The oxidation in step (b) can be carried out, for example, at temperatures in a range from 20 to 150° C., preferably at from 50 to 90° C., more preferably up to 70° C.

The oxidation in step (b) can be carried out, for example, at standard pressure. It is also possible to carry out the oxidation in step (b) at a pressure in the range from 1.1 to 10 bar.

In one embodiment of the present invention, nitric acid or nitrogen oxide, for example $N_2O_4$ or $N_2O_5$, is used in an excess, based on intermediate. Suitable amounts are, for example, from 2 to 10 equivalents, preferably from 3 to 7 equivalents, more preferably from 3 to 6 equivalents, of nitric acid or nitrogen oxide, for example $N_2O_5$, based on intermediate.

In one embodiment of the present invention, step (a) and step (b) are carried out under inert gas. Suitable inert gases are, for example, noble gases and nitrogen. However, it is also possible to work under air.

In many cases, the oxidation in step (b) forms nitrous gases ($NO_x$) which form a gas mixture with inert gas or air. It is preferred to remove nitrous gases which have formed from the offgas in the course of the performance of step (b) of the process according to the invention.

For the removal of the nitrous gases, all known processes for removing $NO_x$ are useful in principle. Suitable processes are, for example, catalytic reduction with hydrocarbons or ammonia, catalytic decomposition over suitable catalysts, absorption into offgas-oxidizing solutions, and absorption in acidic or alkaline solutions.

Suitable offgas-oxidizing solutions in the context of the present invention are, for example, solutions of hydrogen peroxide. Suitable strongly acidic solutions are, for example, solutions comprising nitric acid or sulfuric acid. Suitable alkaline solutions are, for example, aqueous solutions of hydroxides or carbonates, for example, sodium hydroxide or sodium carbonate. Suitable liquids for this washing are, in addition to those already mentioned, especially those which are known per se for the removal of $NO_x$ from offgases, for example aqueous solutions or suspensions comprising magnesium carbonate, magnesium hydroxide, solutions of vanadium compounds in nitrous acid, ammonium sulfide and ammonium bisulfide, limewater, ammonia, hydrogen peroxide and in particular solutions comprising sodium carbonate, sodium bicarbonate or sodium hydroxide.

Suitable processes are mentioned, for example, in M. Thiemann et al. in Ullmann's Encyclopedia, $6^{th}$ Edition, 2000, Electronic Edition, chapter "Nitric Acid, Nitrous Acid, and Nitrogen Oxides", section 1.4.2.3.

In general, the $NO_x$ absorption is effected in devices in which a gas-liquid phase interface is present, by means of which mass and heat transfer between the phases is enabled and which are provided with internal or external devices for heat supply and/or heat removal if required.

The phases in the absorber can be conducted in cocurrent, in countercurrent or a combination of said methods.

According to the invention, the absorption may be carried out in one or more stages.

The absorption is effected in accordance with the invention at temperatures between −20 and 100° C., preferably between 0 and 60° C., more preferably between 0 and 40° C., and at pressures between 0.1 and 100 bar, preferably between 1 and 30 bar.

Possible embodiments of the absorber are columns with trays, for example bubble-cap trays or sieve trays, columns with structured internals, for example structured packings, columns with unstructured internals, for example random packings, or apparatus in which the liquid phase is present in dispersed form, for example by spray-dispensing in nozzles, or a combination of the aforementioned absorbers.

$NO_x$ is removed preferably by absorption in an acidic or an alkaline solution. The absorption is carried out between −20 and 120° C., in particular between −10 and 75° C., preferably between 0 and 60° C., for example between 0 and 40° C., and at a pressure between 0.2 and 100 bar, in particular between 0.5 and 50 bar, preferably between 1 and 10 bar.

When the $NO_x$ concentration in the offgas is more than 1% by volume, the offgas-oxidizing solution used is preferably aqueous nitric acid having an $HNO_3$ content between 0.1 and 69% by weight, preferably between 1 and 10% by weight. It is advantageous in this context that the $NO_x$ depletion in the gas phase is accompanied by the preparation of nitric acid with from 1 to 69% by weight of $HNO_3$. In the context of further utility, preference is given to preparing nitric acid having from 30 to 60% by weight of $HNO_3$.

In one embodiment of the present invention, the offgas scrubbing can preferably be followed by a chemical scrubbing, more preferably with sodium carbonate solution or sodium hydroxide solution.

In the context of the present invention, for example, the chemical carbonate scrubbing can be replaced by a selective catalytic reduction with ammonia in which N₂O behaves inertly. This so-called SCR-DeNOx or DeNOx technology is described, for example, in Ullmann's Encyclopedia of Chemical Technology, chapter "Air", section 7.2.3.1. *"Catalytic Reduction of Nitrogen Oxides in Flue Gases and Process Off-Gases"* by J. Wolf et al., 6th edition (Online Edition), 2000. In this preferred embodiment of the present invention, it is possible to attain $NO_x$ concentrations of less than 100 ppm, preferably less than 50 ppm, for example less than 25 ppm and more preferably of up to 5 ppm.

It is possible in one specific variant of the present invention to remove nitrous gases which form from the gas mixture with the aid of a basic gas scrubber, for example with the aid of an offgas scrubber filled with sodium hydroxide solution.

The sequence of addition of nitric acid, intermediate and catalyst, and initiator if appropriate, is uncritical per se. However, preference is given to adding nitric acid, catalyst and initiator if appropriate to intermediate, if appropriate mixed with water from step (a).

In one embodiment of the present invention, nitric acid, intermediate, if appropriate mixed with water from step (a), and catalyst and if appropriate initiator are mixed at temperatures in the range from 20 to 100° C.; preferably from 50 to 90° C., more preferably from 65 to 75° C.

In one embodiment of the present invention, step (b) is carried out over a period in the range from 1 hour to 10 hours, preferably up to 5 hours.

Step (a) and (b) can be followed by workup. To this end, desired compound of the general formula I is removed from the reaction mixture which forms as such or in the form of one of its salts, preferably as the mono(alkali metal) salt.

Salts of compound of the general formula I are, for example, salts of alkali metals such as lithium, rubidium and in particular potassium and sodium, in particular mono(alkali metal) salts, for example monosodium salts and monopotassium salts.

In one embodiment of the present invention, it is possible to effect workup by initially cooling, for example to temperatures in the range from 25 to 40° C. or to room temperature, and then to remove compound of the general formula I which precipitates by suitable solid-liquid separation methods, in particular by decanting or by filtration. After the removal of compound of the general formula I, it is possible in accordance with the invention to wash tetracarboxylic acid prepared, for example with water or with carboxylic acid which is liquid at room temperature, for example formic acid or acetic acid, especially with glacial acetic acid, and to dry it.

The reaction mixture can be neutralized partially with base to form salts, for example with basic alkali metal salts. Suitable basic alkali metal salts are the hydrogen-carbonates, carbonates and in particular the hydroxides of alkali metals such as lithium, rubidium and in particular potassium and sodium. When the reaction mixture is to be neutralized partially with base, any remaining nitric acid and not more than one carboxyl group of tetracarboxylic acid of the general formula I prepared in accordance with the invention are typically neutralized.

The process according to the invention affords, for example, particularly pure tetracarboxylic acid of the general formula I.

The present invention further provides mixtures of tetracarboxylic acid of the general formula I or its salt

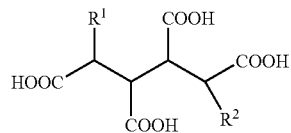

where the variables are defined as follows:

$R^1$, $R^2$ are different or preferably the same and are selected from phenyl, $C_1$-$C_{10}$-alkyl branched or preferably unbranched, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl, more preferably $C_1$-$C_4$-alkyl such as methyl, ethyl, n-propyl, n-butyl, and most preferably hydrogen, and in the range from 0.1 ppm to 0.1% by weight of compound of the general formula IV

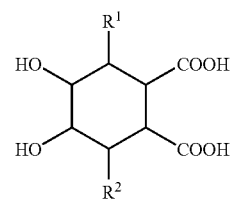

in which the variables are each as defined above.

Tetracarboxylic acid of the general formula I and mixtures characterized above can be obtained particularly conveniently by the process according to the invention.

Tetracarboxylic acid of the general formula I prepared in accordance with the invention and mixtures characterized above do not exhibit any discoloration perceptible with the naked eye in the course of heating to, for example, temperatures in the range from 120 to 145° C., even for more than 30 minutes.

Tetracarboxylic acid of the general formula I prepared in accordance with the invention and mixtures characterized above are suitable for treating textiles, in particular cotton. Tetracarboxylic acid of the general formula I prepared in accordance with the invention and above-characterized mixtures are very particularly suitable for anticrease finishing of textiles, for example cotton. The present invention therefore further provides for the use of tetracarboxylic acids of the general formula I prepared in accordance with the invention and mixtures characterized above for the anticrease finishing of textiles. The present invention further provides a process for the anticrease finishing of textiles using tetracarboxylic acids of the general formula I prepared in accordance with the invention and mixtures characterized above.

Textiles should be understood to mean two- or three-dimensional substrates made of fibrous material, for example fibers, yarns, threads, knits, wovens, nonwovens and garments made of cellulosic material, for example cotton, jute, flax, hemp and ramie, and also cotton blends with polyester, modified polyester, polyamide, polyacrylonitrile, triacetate, acetate, polycarbonate, polypropylene, polyvinyl chloride, viscose, silk.

For example, it is thus possible to allow one or more tetracarboxylic acids of the general formula I prepared in accordance with the invention or one or more mixtures characterized above to act on appropriate cotton or cotton/synthetic fiber blend fabric in amounts of from 0.5 to 10 mol % based on anhydroglucose in cotton. Such an action can be accomplished in the presence of a crosslinking catalyst, for example $NaH_2PO_2$. Subsequently, drying can be effected at temperatures in the range of, for example, from 120 to 180° C., preferably from 145 to 165° C., especially with avoidance of mechanical tension. Tetracarboxylic acids of the general formula I prepared in accordance with the invention and mixtures characterized above for the anticrease finishing of textiles cause crosslinking of the cellulose fibers and thus improved freedom from creases.

It is also possible to use tetracarboxylic acids of the general formula I prepared in accordance with the invention or mixtures characterized above in combination with oligomaleic acid phosphonates for the anticrease finishing of textiles by process conditions which are known in principle, for example, from WO 03/33811.

The invention is illustrated by working examples.

Preliminary remark: cis-$\Delta^4$-tetrahydrophthalic anhydride was prepared by reacting maleic anhydride with butadiene according to GB 1,032,883.

1. Reaction of cis-$\Delta^4$-tetrahydrophthalic acid with isolation of the intermediate after step (a)

A 500-ml three-neck flask with stirrer, reflux condenser and internal thermometer was initially charged with 91.4 g of cis-$\Delta^4$-tetrahydrophthalic anhydride and 59.1 g of water. The mixture was heated with stirring to an internal temperature of from 95 to 100° C. The mixture was stirred at 95° C. for 30 minutes and then cooled to 80° C. Afterward, 82.5 g of 50% by weight aqueous $H_2O_2$ solution were added within 15 minutes and the mixture was then stirred at 80° C. for four hours. Afterward, a rotary evaporator was used to distill off to dryness. 118 g of trans-4,5-dihydroxyhexahydrophthalic acid remained as a colorless solid.

A 500-ml four-neck flask with stirrer, dropping funnel, reflux condenser, outlet to an offgas scrubber charged with sodium hydroxide solution and internal thermometer was initially charged with 112 g of 65% by weight aqueous nitric acid and 22 mg of ammonium metavanadate $NH_4VO_3$, and heated with stirring to 65° C. The trans-4,5-dihydroxyhexahydrophthalic acid obtained as described was added in portions. Red-brown nitrous gases evolved. The mixture was stirred at 65° C. for a further 4 hours. The reaction mixture thus obtained was then cooled to room temperature. meso-1,2,3,4-Butanetetracarboxylic acid separated out as a colorless solid which was filtered off, washed with glacial acetic acid and dried under reduced pressure. The yield was 80% based on trans-4,5-dihydroxyhexahydrophthalic acid. Even with the aid of gas chromatography, it was not possible to detect any impurities.

2. Reaction of cis-$\Delta^4$-tetrahydrophthalic acid without isolation of the intermediate after step (a)

A 500-ml four-neck flask with stirrer, dropping funnel, reflux condenser, internal thermometer and outlet to an offgas scrubber charged with sodium hydroxide solution was initially charged with 91.3 g of cis-$\Delta^4$-tetrahydrophthalic anhydride and 59.6 g of water. The mixture was heated with stirring to an internal temperature of from 95 to 100° C. The mixture was stirred at 95° C. for 30 minutes and then cooled to 80° C. Afterward, 81.8 g of 50% by weight aqueous $H_2O_2$ solution were added within 15 minutes and the mixture was then stirred at 80° C. for four hours. The mixture was then cooled to 65° C. and 22 mg of ammonium metavanadate were added. 345 g of 65% by weight aqueous nitric acid were added with stirring. Red-brown nitrous gases evolved. The mixture was stirred at 65° C. for 4 hours. The reaction mixture thus obtained was then cooled to room temperature. meso-1,2,3,4-Butanetetracarboxylic acid separated out as a colorless solid which was filtered off, washed with glacial acetic acid and dried under reduced pressure. The isolated yield was 56% based on cis-$\Delta^4$-tetrahydrophthalic anhydride. Even with the aid of gas chromatography, it was not possible to detect any impurities.

By concentration of the mother liquors and a further crystallization, it was possible to obtain additional meso-1,2,3,4-butanetetracarboxylic acid which was, though, no longer as pure.

3. Reaction of cis-$\Delta^4$-tetrahydrophthalic acid without isolation of the intermediate after step (a), removal of water by distillation A 500-ml four-necked flask with stirrer, dropping funnel, reflux condenser, internal thermometer and outlet to an offgas scrubber charged with sodium hydroxide solution was initially charged with 91.3 g of cis-$\Delta^4$-tetrahydrophthalic anhydride and 59.6 g of water. The mixture was heated with stirring to an internal temperature of from 95 to 100° C. The mixture was stirred at 95° C. for 30 minutes and then cooled to 80° C. Afterward, 81.8 g of 50% by weight aqueous $H_2O_2$ solution were added within 15 minutes and the mixture was then stirred at 80° C. for four hours. In the course of this, about 5 g of water distilled off but the flask contents remained liquid. The mixture was then cooled to 65° C. and 56 mg of ammonium metavanadate were added. 345 g of 65% by weight aqueous nitric acid were added with stirring. Red-brown nitrous gases evolved. The mixture was stirred at 65° C. for 4 hours. The reaction mixture thus obtained was then cooled to room temperature. meso-1,2,3,4-Butanetetracarboxylic acid separated out as a colorless solid which was filtered off, washed with glacial acetic acid and dried under reduced pressure. The yield was 81% based on cis-$\Delta^4$-tetrahydrophthalic anhydride. Even with the aid of gas chromatography, it was not possible to detect any impurities.

4. Reaction of cis-$\Delta^4$-tetrahydrophthalic acid with addition of catalyst for step (b) before step (a) without isolation of the intermediate after step (a)

A 500-ml four-necked flask with stirrer, dropping funnel, distillation apparatus, internal thermometer and outlet to an offgas scrubber charged with sodium hydroxide solution was initially charged with 91.3 g of cis-$\Delta^4$-tetrahydrophthalic anhydride, 26 mg of ammonium metavanadate and 59.6 g of water. The mixture was heated with stirring to an internal temperature of from 95 to 100° C. The mixture was stirred at 95° C. for 30 minutes and then cooled to 80° C. Afterward, 81.8 g of 50% by weight aqueous $H_2O_2$ solution were added within 15 minutes and the mixture was then stirred at 80° C. for four hours. In the course of this, about 5 g of water distilled off but the flask contents remained liquid. The mixture was then cooled to 65° C. 345 g of 65% by weight aqueous nitric acid were added with stirring. Red-brown nitrous gases evolved. The mixture was stirred at 65° C. for 4 hours. The reaction mixture thus obtained was then cooled to room temperature. meso-1,2,3,4-Butanetetracarboxylic acid separated out as a colorless solid which was filtered off, washed with glacial acetic acid and dried under reduced pressure. The yield was 45% based on cis-Δ⁴-tetrahydrophthalic anhydride. Even with the aid of gas chromatography, it was not possible to detect any impurities.

By concentration of the mother liquors and a further crystallization, it was possible to obtain additional meso-1,2,3,4-butanetetracarboxylic acid which was, though, no longer as pure.

What is claimed is:

1. A process for preparing one or more tetracarboxylic acids of formula I

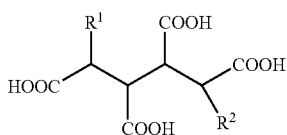

I or salts thereof, wherein at least one compound of formula II a or II b

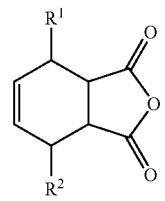

IIa

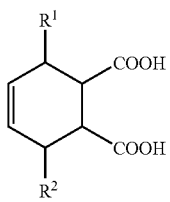

IIb is first reacted with at least one epoxidation reagent and then oxidized with nitric acid or at least one nitrogen oxide, where $R^1$, $R^2$ are the same or different and are selected from the group consisting of hydrogen, phenyl and $C_1$-$C_{10}$-alkyl, wherein the at least one epoxidation reagent is hydrogen peroxide and the reaction of the at least one compound of formula IIa or IIb with at least one epoxidation reagent is carried out without the use of a catalyst.

2. The process according to claim 1, wherein $R^1$, $R^2$ in formula I, formula IIa and IIb are each the same and are hydrogen.

3. The process according to claim 1, wherein the oxidation with nitric acid or at least one nitrogen oxide is carried out in the presence of a catalyst.

4. The process according to claim 1, wherein the oxidation with nitric acid or at least one nitrogen oxide is carried out in the presence of a catalyst which comprises vanadium.

5. The process according to claim 1, wherein the oxidation with nitric acid or at least one nitrogen oxide follows the reaction of the at least one compound of formula IIa or IIb with at least one epoxidation reagent without isolation of an intermediate.

6. The process according to claim 1, wherein, after the reaction of the at least one compound of formula IIa or IIb with at least one epoxidation reagent and the oxidation with nitric acid or at least one nitrogen oxide have been carried out, the tetracarboxylic acid of formula I is converted to its salt.

7. The process according to claim 6, wherein the salt is a mono(alkali metal) salt.

8. The process according to claim 1, wherein the oxidation with nitric acid or at least one nitrogen oxide is carried out at temperatures in the range from 20 to 70° C.

9. The process according to claim 1, wherein the one or more tetracarboxylic acids obtained by said process have no detectable amount of impurities as determined by gas chromatography.

* * * * *